(12) United States Patent
Sobek et al.

(10) Patent No.: US 8,476,053 B2
(45) Date of Patent: Jul. 2, 2013

(54) STABILIZED AQUEOUS ALPHA-GALACTOSIDASE COMPOSITION AND METHODS RELATING THERETO

(75) Inventors: Harald Sobek, Penzberg (DE); Manfred Schmidt, Penzberg (DE); Rainer Mueller, Penzberg (DE); Werner Hoelke, Penzberg (DE); Johann-Peter Thalhofer, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 275 days.

(21) Appl. No.: 12/762,465

(22) Filed: Apr. 19, 2010

(65) Prior Publication Data
US 2010/0273235 A1   Oct. 28, 2010

(30) Foreign Application Priority Data
Apr. 24, 2009  (EP) .................................. 09005753

(51) Int. Cl.
C12N 9/00 (2006.01)
C12N 9/40 (2006.01)
C12N 1/20 (2006.01)
C12N 15/00 (2006.01)

(52) U.S. Cl.
USPC ...... 435/208; 435/183; 435/252.3; 435/320.1

(58) Field of Classification Search
None
See application file for complete search history.

(56) References Cited

FOREIGN PATENT DOCUMENTS
WO   2007/053565 A3   5/2007

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
European Search Report issued May 19, 2010 in European Patent Application No. 10003549.2.
Berg, Jan-Olof et al., Purification of Glycoside Hydrolases from *Bacteroides fragilis*, Applied and Environmental Microbiology, Jul. 1980, pp. 40-47, vol. 40, No. 1.
Gherardini, Frank et al., Purification and Characterization of Two α-Galactosidases Associated with Catabolism of Guar Gum and Other α-Galactosides by *Bacteroides ovatus*, Journal of Bacteriology, Feb. 1985, pp. 500-506, vol. 161, No. 2.
Ishibashi, Matsujiro et al., Is arginine a protein-denaturant?, Protein Expression and Purification, 2005, pp. 1-6, vol. 42.
Liu, Qiyong P. et al., Bacterial glycosidases for the production of universal red blood cells, Nature Biotechnology, Apr. 2007, pp. 454-464, vol. 25, No. 4.
Shiraki, Kentaro et al., Biophysical Effect of Amino Acids on the Prevention of Protein Aggregation, Journal of Biochemistry, 2002, pp. 591-595, vol. 132, No. 4.
Tsumoto, Kouhei et al., Role of Arginine in Protein Refolding, Solubilization, and Purification, Biotechnol. Prog. Sep. 11, 2004, pp. 1301-1308, vol. 20, No. 5.
Liu Caiqin et al, Study on Improvement of Stability of Alpha-Galactosidase, Food and Fermentation Industries, vol. 33, No. 11, pp. 26-29, (2007).
Liu et al., exo-alpha-galactosidase variant B gene [*Bacteroides fragilis*], GenBank; CAJ33351, (2008).
First Office Action of co-pending Chinese application No. 201010170755.8 mailed Aug. 24, 2011.
Arakawa, Tsutomu et al., "Aggregation Suppression of Proteins by Arginine During Thermal Unfolding," Protein & Peptide Letters, 2006, pp. 921-927, vol. 13.
Altschul, Stephan F. et al., "Basic Local Alignment Search Tool," Journal of Molecular Biology, 1990, pp. 403-410, vol. 215.
Bakunina, I. Yu et al., "α-Galactosidase of Marine Bacteria Pseudoalteromonas Sp. KMM 701," Biochemistry (Mosc.) 1998, pp. 1420-1427, vol. 63, No. 10, English Abstract.
Davies, Gideon J. et al., "Recent structural insights into the expanding world of carbohydrate-active enzymes," Current Opinion in Structural Biology, 2005, pp. 637-645, vol. 15.
Pearson, William R. and Lipman, David J., "Improved tools for biological sequence comparison," Proceedings of the National Academy of Sciences USA, Apr. 1988, pp. 2444-2448, vol. 85.
Smith, Temple F. and Waterman, Michael S., "Comparison of Biosequences," Advances in Applied Mathematics, 1981, pp. 482-489, vol. 2.

* cited by examiner

*Primary Examiner* — Christian Fronda
(74) *Attorney, Agent, or Firm* — Dinsmore & Shohl LLP (57) ABSTRACT

The present invention provides an aqueous composition comprising a protein with enzymatic activity of alpha-galactosidase. The present invention further provides a method of stabilizing an aqueous composition comprising a protein with enzymatic activity of alpha-galactosidase, and a method of preparing a purified aqueous composition comprising the protein with enzymatic activity of alpha-galactosidase.

28 Claims, 3 Drawing Sheets

MRVYDISQFGLKANSKKNASPVVRKAIAKIKAECRDGEKVILRFPAGRYNFHEAG
STVREYYISNHDQDNPKKVGIALEDMKNLTIDGQGSEFVFYGRMIPVSLLRSENC
VLKNFSIDFEQPHIAQVQVVENDPEKGITFEPAPWVDYRISKDSVFEGLGEGWVM
RYSWGIAFDGKTKHVVYNTSDIGCPTKGAFEVAPRRICSPKWKDARLVPGTVVAM
RGWGRPTPGIFMSHDVNTSLLDVKVHYAEGMGLLAQLCEDITLDGFGVCLKGDND
PRYFTTQADATHFSGCKGKIVSKNGLYEGMMDDAINVHGTYLKVIKRVDDHTLIG
RYMHDQSWGFEWGRPGDDVQFVRSETMELIGKQNQITAIRPYDKGEIRGAREFSI
TFKEAIDPAINEKSGFGIENLTWTPEVLFAGNTIRNNRARGTLFSTPKKTVVEDN
LFDHTSGTAILLCGDCNGWFETGACRDVTIRRNRFINALTNMFQFTNAVISIYPE
IPNLKDQQKYFHGGKDGGIVIEDNEFDTFDAPILYAKSVDGLIFRNNVIKTNTEF
KPFHWNKDRFLLERVTNVKISE (SEQ ID NO: 1)

SEQUENCE LISTING

<160> NUMBER OF SEQ ID NOS: 2

<210> SEQ ID NO 1
<211> LENGTH: 572
<212> TYPE: PRT
<213> ORGANISM: Bacteroides fragilis

<400> SEQUENCE: 1

```
Met Arg Val Tyr Asp Ile Ser Gln Phe Gly Leu Lys Ala Asn Ser Lys
1               5                   10                  15

Lys Asn Ala Ser Pro Val Val Arg Lys Ala Ile Ala Lys Ile Lys Ala
            20                  25                  30

Glu Cys Arg Asp Gly Glu Lys Val Ile Leu Arg Phe Pro Ala Gly Arg
        35                  40                  45

Tyr Asn Phe His Glu Ala Gly Ser Thr Val Arg Glu Tyr Tyr Ile Ser
    50                  55                  60

Asn His Asp Gln Asp Asn Pro Lys Lys Val Gly Ile Ala Leu Glu Asp
65                  70                  75                  80

Met Lys Asn Leu Thr Ile Asp Gly Gln Gly Ser Glu Phe Val Phe Tyr
                85                  90                  95

Gly Arg Met Ile Pro Val Ser Leu Leu Arg Ser Glu Asn Cys Val Leu
            100                 105                 110

Lys Asn Phe Ser Ile Asp Phe Glu Gln Pro His Ile Ala Gln Val Gln
        115                 120                 125

Val Val Glu Asn Asp Pro Glu Lys Gly Ile Thr Phe Glu Pro Ala Pro
    130                 135                 140

Trp Val Asp Tyr Arg Ile Ser Lys Asp Ser Val Phe Glu Gly Leu Gly
145                 150                 155                 160

Glu Gly Trp Val Met Arg Tyr Ser Trp Gly Ile Ala Phe Asp Gly Lys
                165                 170                 175

Thr Lys His Val Val Tyr Asn Thr Ser Asp Ile Gly Cys Pro Thr Lys
            180                 185                 190
```

```
Gly Ala Phe Glu Val Ala Pro Arg Arg Ile Cys Ser Pro Lys Trp Lys
            195                 200                 205

Asp Ala Arg Leu Val Pro Gly Thr Val Val Ala Met Arg Gly Trp Gly
        210                 215                 220

Arg Pro Thr Pro Gly Ile Phe Met Ser His Asp Val Asn Thr Ser Leu
225                 230                 235                 240

Leu Asp Val Lys Val His Tyr Ala Glu Gly Met Gly Leu Leu Ala Gln
                245                 250                 255

Leu Cys Glu Asp Ile Thr Leu Asp Gly Phe Gly Val Cys Leu Lys Gly
            260                 265                 270

Asp Asn Asp Pro Arg Tyr Phe Thr Thr Gln Ala Asp Ala Thr His Phe
        275                 280                 285

Ser Gly Cys Lys Gly Lys Ile Val Ser Lys Asn Gly Leu Tyr Glu Gly
    290                 295                 300

Met Met Asp Asp Ala Ile Asn Val His Gly Thr Tyr Leu Lys Val Ile
305                 310                 315                 320

Lys Arg Val Asp Asp His Thr Leu Ile Gly Arg Tyr Met His Asp Gln
                325                 330                 335

Ser Trp Gly Phe Glu Trp Gly Arg Pro Gly Asp Val Gln Phe Val
            340                 345                 350

Arg Ser Glu Thr Met Glu Leu Ile Gly Lys Gln Asn Gln Ile Thr Ala
        355                 360                 365

Ile Arg Pro Tyr Asp Lys Gly Glu Ile Arg Gly Ala Arg Glu Phe Ser
370                 375                 380

Ile Thr Phe Lys Glu Ala Ile Asp Pro Ala Ile Asn Glu Lys Ser Gly
385                 390                 395                 400

Phe Gly Ile Glu Asn Leu Thr Trp Thr Pro Glu Val Leu Phe Ala Gly
            405                 410                 415

Asn Thr Ile Arg Asn Asn Arg Ala Arg Gly Thr Leu Phe Ser Thr Pro
        420                 425                 430

Lys Lys Thr Val Val Glu Asp Asn Leu Phe Asp His Thr Ser Gly Thr
    435                 440                 445

Ala Ile Leu Leu Cys Gly Asp Cys Asn Gly Trp Phe Glu Thr Gly Ala
    450                 455                 460

Cys Arg Asp Val Thr Ile Arg Arg Asn Arg Phe Ile Asn Ala Leu Thr
465                 470                 475                 480

Asn Met Phe Gln Phe Thr Asn Ala Val Ile Ser Ile Tyr Pro Glu Ile
                485                 490                 495

Pro Asn Leu Lys Asp Gln Gln Lys Tyr Phe His Gly Gly Lys Asp Gly
            500                 505                 510

Gly Ile Val Ile Glu Asp Asn Glu Phe Asp Thr Phe Asp Ala Pro Ile
        515                 520                 525

Leu Tyr Ala Lys Ser Val Asp Gly Leu Ile Phe Arg Asn Asn Val Ile
530                 535                 540

Lys Thr Asn Thr Glu Phe Lys Pro Phe His Trp Asn Lys Asp Arg Phe
545                 550                 555                 560

Leu Leu Glu Arg Val Thr Asn Val Lys Ile Ser Glu
                565                 570
```

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

```
<400> SEQUENCE: 2

His His His His His His
1               5
```

STABILIZED AQUEOUS ALPHA-GALACTOSIDASE COMPOSITION AND METHODS RELATING THERETO

RELATED APPLICATIONS

This application claims priority to European application EP 09005753.0 filed Apr. 24, 2009.

SEQUENCE LISTING

The instant application contains a Sequence Listing which has been submitted via EFS-Web and is hereby incorporated by reference in its entirety. Said ASCII copy, created on Mar. 25, 2010, is named 25954US.txt, and is 5,528 bytes in size.

FIELD OF THE INVENTION

The present invention relates to an aqueous composition comprising a protein with enzymatic activity of alpha-galactosidase. The present invention further relates to a method of stabilizing an aqueous composition comprising a protein with enzymatic activity of alpha-galactosidase, as well as to a method of preparing a purified aqueous composition comprising said protein with enzymatic activity of alpha-galactosidase.

The ABO blood group system, discovered in 1900, plays an important role in human blood transfusion and, consequently, in transfusion medicine. The ABO blood system is based on the presence or absence of the blood group antigens A and B, respectively. The corresponding blood group carbohydrate structures, designated ABH, are found on the surface of erythrocytes, in particular at the termini of oligosaccharide chains on glycoproteins and glycolipids. That is, the A antigen which is found on blood group A erythrocytes is specified by a terminal α-1,3-linked N-acetylgalactosamine (GalNAc), while the B antigen on blood group B is specified by a terminal α-1,3-linked galactose (Gal) monosaccharide as the immunodominant monosaccharide.

Enzymes active on carbohydrates are widely spread in nature and have found applications in many biotechnological and pharmaceutical processes (Davies et al., 2005). The enzymatic removal of the blood group ABO antigens to develop universal red blood cells was a pioneering vision originally proposed more than 25 years ago. The enzymatic removal of the α-1,3-linked N-acetylgalactosamine and α-1,3-linked galactose monosaccharides from group A and B blood cells, respectively, thus offers an attractive approach to improve transfusion safety and the overall blood supply. Originally, it was envisioned to enzymatically convert the A and B antigens on red blood cells to H antigens, respectively, by the use of exoglycosidases for the selective removal of the α-GalNAc and α-Gal residues of the immunodominant A and B trisaccharide antigens. Especially, alpha-N-acetyl-galactosaminidases and alpha-galactosidases are of particular interest in the enzymatic conversion of blood group A, B and AB red blood cells (WO 03/027245 A2). While the exoglucosidase alpha-N-acetyl-galactosaminidase (A-zyme) specifically hydrolyzes terminal α-1,3-GalNAc residues on group A red blood cells, the exoglucosidase alpha-galactosidase (B-zyme) specifically hydrolyzes terminal α-1,3-galactose residues on group B red blood cells. Both enzymatic reactions result in the formation of the common H structure found on red blood cells of group 0.

For the conversion of group B red blood cells, an alpha-galactosidase derived from green coffee beans was first used. It was demonstrated that enzymatic conversion of red blood cells is feasible, and, moreover, that converted blood cells can function in transfusions, clinical implementation was not possible due to the large quantities of enzyme required. More recently, the use of an alpha-galactosidase from the marine bacterium *Pseudoalteromonas* spec. to remove alpha-1,3-bound galactose residues from erythrocytes of blood group B was described (Bakunina et al., 1998). In addition, two bacterial glycosidase gene families that provide enzymes capable of efficiently removing A and B antigens at neutral pH with low consumption of recombinant enzymes were reported (Liu et al., 2007). Among these was a recombinant N-terminal fragment of the alpha-galactosidase derived from the bacterial organism *Bacteroides fragilis*.

Recombinant DNA technology has revolutionized biochemistry since it came into being in the 1970s. On the one hand, due to the sensitivity of the recently developed microchemical techniques in combination with the amplification afforded by gene cloning and polymerase chain reaction (PCR), endogenous proteins from cells or tissues of any kind as well as their corresponding messenger RNAs can since serve as a starting point for the isolation and cloning of their respective genes. On the other hand, recombinant DNA technology paved the way for the efficient large scale production of thereby identified and isolated genes, since it enabled the introduction of a DNA encoding a protein of interest into host organisms or into cells grown in culture for the purpose of recombinant protein expression. In particular, bacteria are considered as ideal hosts for both gene amplification and gene expression since they represent easy to handle factories for the production of a wide range of prokaryotic and eukaryotic proteins. The expression of recombinant heterologous proteins in a bacterial host cell, however, often results in the formation of inclusion bodies containing the protein of interest in aggregated and insoluble form, with the consequence that the expressed protein is not accessible for further biochemical purification. In this case, the recovery of recombinant proteins requires the solubilization of the inclusion bodies and refolding of the proteins into their active structure.

Alpha-galactosidase enzymes, which are classified as EC 3.2.1.22 by the Enzyme Commission of the International Union of Biochemistry, are endogenously expressed by a variety of microorganisms, plants and animals. The provision of aqueous enzyme compositions in vitro, however, is very difficult due to the rapid decrease in alpha-galactosidase activity when stored in aqueous solution. In particular, it is a general problem in the art that recombinantly expressed alpha-galactosidases form insoluble precipitates in the absence of salt, i.e. in buffers with low conductivity. This precipitation occurs rapidly, turns out to be irreversible, and is favoured in the context of high protein concentrations. The known purification methods of alpha-galactosidase at low protein concentrations (to prevent precipitation), however, is not a suitable option for an economically useful production process. So far, precipitation of the enzyme has usually been prevented by the addition of salt in a suitable concentration. Therefore, a buffer containing high salt concentration is indispensable for stabilization of the enzyme in solution. For example, a buffer which is commonly used for storage of alpha-galactosidase enzyme consists of 25 mM sodium phosphate and 0.3 M NaCl, pH 7.0. However, such high salt buffer conditions, do not allow for some of the biochemical purification methods which might be desirable such as, e.g., cation-exchange chromatography which requires binding of the protein to a column at low salt conditions. Cation-exchange chromatography represents an essential tool in order to achieve a substantially pure alpha-galactosidase composition, since it is the most favorable method for the efficient elimination of degradation products and/or other contaminating proteins.

Alternatively, the protein of interest could be purified by the means of anion-exchange chromatography. That is, proteins with an isoelectric point in the acidic pH range can be bound to anion exchange resins at alkaline pH values. Alpha-galactosidase, however, in particular the alpha-galactosidase from *Bacteriodes fragilis* as reported by Liu et al. (2007) having an isoelectric point of pI 6.72, is soluble but unstable in buffers with alkaline pH values (e.g., pH at about ≧9.0 or higher). The incubation of the enzyme in buffers with an alkaline pH therefore led to an irreversible loss of enzyme activity. Consequently, purification of the protein by means of anion exchange chromatography at pH values of about pH≧9.0 did not seem to be an option for a purification strategy of alpha-galactosidase (also designated "B-zyme" in the context of the present invention).

Therefore, it was one object of the present invention to provide a method of stabilizing an aqueous composition comprising a protein with alpha-galactosidase activity to provide a stable alpha-galactosidase composition for storage and further processing and methods of producing the same.

SUMMARY OF THE INVENTION

A variety of agents are known in the art to facilitate the recovery of proteins from inclusion bodies and to support solubilization and protein refolding. These include, among others, e.g., Chaotropic salts, urea, and non detergent sulfobetaines. In the context of the present invention, it was surprisingly found that alpha-galactosidase is stabilized in solution in the presence of arginine at a concentration of above 100 mM, in particular at a concentration of at least 150 mM. Significantly, stabilization of the protein was not achieved by any of the other agent tested in the context of the present invention at various concentrations.

Arginine has been used for improving the refolding efficiency, or to suppress the aggregation of proteins (Arakawa et al., 2006; Ishibashi et al., 2005). Moreover, the role of arginine in heat-induced and dilution-induced aggregation of proteins has been described (Shiraki et al., 2002). Arginine has further been implicated in protein refolding, solubilization and purification, and it has been reported that 0.1 to 1 M arginine can be included in solvents used for refolding of proteins by dialysis or dilution. Moreover, arginine at a concentration of 0.5 to 2 M can be used to extract active, folded proteins from insoluble pellets obtained after lysis of *E. coli* cells (Tsumoto et al, 2004).

The stabilization with arginine provides a clear technical advantage, since it allows for the concentration of the enzyme to high levels in solution without loss of material due to protein precipitation. Consequently, the stabilization with arginine allows for the provision of an alpha-galactosidase composition suitable for long-term storage and further processing. Secondly, the stabilization in the presence of arginine allows for the economical application of a high yield purification scheme including ion-exchange chromatography, in particular cation ion-exchange chromatography. Consequently, the stabilization of the enzyme in the presence of arginine allows for the provision of a composition comprising purified alpha-galactosidase.

DETAILED DESCRIPTION OF THE INVENTION

In a first aspect, the present invention provides an aqueous composition comprising a protein with enzymatic activity of alpha-galactosidase, characterized in that said composition comprises arginine at a concentration of above 100 mM, in particular at a concentration of at least 150 mM.

The term "aqueous composition" as used herein refers to any kind of water-based solution containing the protein of interest. Water-based solution or aqueous solution means that the solvent is predominantly water (more that 50%, 60%, 75%, 80%, preferably more than 90%, more preferably more than 95%, or even 100% of the solvent is water). Additionally, one or more suitable solubilizers such as DMSO, ethanol etc. may be present. In addition to the protein with enzymatic activity of alpha-galactosidase further compounds may be present in the aqueous composition such as salts, other protein, cellular components, ingredients of growth media etc. In particular, the aqueous composition according to the present invention might comprise, in addition to a protein with enzymatic activity of alpha-galactosidase, any sort of mono-, di- or trivalent salt ions, including, but not limited to, $Na^+$, $K^+$, $Mg^{++}$, $PO_4^{3-}$, $Ca^{++}$, $Cl^-$, and alike, as well as any kind of cellular and/or nuclear components including, e.g., cellular and/or nuclear proteins, cellular and/or nuclear DNA, and cellular and/or nuclear RNA molecules. Moreover, the aqueous composition of the present invention might be any cellular extract derived from an organism containing the protein of interest in either purified or non-purified form. Such a cellular extracts can either be derived from the organism as a whole, from a particular tissue of said organism, from a variety of tissues thereof, or from any kind of cells, e.g., cultivated in cell culture. Cell extracts prepared from whole organisms or tissues can be made with or without an initial fractionation and/or centrifugation step(s). In addition, the aqueous composition of the present invention might further comprise any additive(s) which might be helpful for stabilizing the protein of interest and/or protecting the latter from proteolytic degradation including, but not limited to, e.g., specific protease inhibitors and protease inhibitor cocktails. Suitable additives which serve in the stabilization of proteins are well known to the skilled person in the art (see, e.g., Sucker et al., 1991), and include, e.g., physiological salines, Ringer dextrose, Ringer lactate, demineralized water, stabilizers, antioxidants, complexing agents, and/or antimicrobial compounds. The composition of the present invention might further comprise glycerol, sucrose, glucose, vitamins, or reducing agents such as, e.g., DTT or beta-mercaptoethanol. An aqueous composition according to the present invention is, e.g., exemplified in Example 5.

Preferably, the aqueous composition comprising a protein with enzymatic activity of alpha-galactosidase is a clear solution and a solution with precipitate or an opal solution, wherein the precipitate or turbidity results from the protein with enzymatic activity of alpha-galactosidase, would not be regarded as aqueous composition comprising a protein with enzymatic activity of alpha-galactosidase according to the invention.

One way to determine clarity/turbidity is by visual inspection, i.e. inspection by eye. Another way of determination is measurement of light attenuation with a photometer. In this regard, the term "Optical density" (also referred to as "OD") denotes a unitless measure of the transmittance of an optical element for a given length at a given wavelength $\lambda$:

$$OD_\lambda = \log_{10} O = -\log_{10} T = -\log_{10}(I/I_0)$$

whereby
O=the per-unit opacity
T=the per-unit transmittance
$I_0$=the intensity of the incident light beam
I=the intensity of the transmitted light beam.

The higher the optical density, the lower the transmittance. Owing to the scattering of a light beam focused on the particles the optical density of a suspension or a colloid is increased compared to a clear solution.

A preferred way to determine turbidity is to measure the scattered light. To this end, a light scattering photometer is used frequently. Depending on the direction from which light scatter is detected and quantified, there are several types of scattered light photometers known to the art. In principle, all can be used for quantitative assessment of turbidity in liquid samples. The term "light scatter" collectively includes both the scatter of light waves by particles in the sample, as well as reflection by particulate matter in the sample. Back Scatter is defined as less than 90°; toward the light source. Forward scatter is defined as less than 90° away from, or in the same general direction as the light source. A majority of turbidity units of measure used today are based on 90° side scatter measurement techniques.

The intensity of the scattered light depends on the amount of the non-dissolved (particulate) matter in the heterogeneous mixture and can be described by:

$$F = I_0 \cdot \Phi \cdot (2.303 \cdot \epsilon \cdot c \cdot d)$$

whereby
F is the intensity of the scattered light
$I_0$ is the intensity of the incoming light beam
$\Phi$ is the ratio of emitted versus absorbed photons
$\epsilon$ is the molar absorption coefficient of the particulate substance in the mixture
c is the amount of the particulate substance per volume of the liquid sample (heterogeneous mixture) in the cuvette
d is the thickness of the space in the cuvette.

For example, for determining the clarity/turbidity of the composition of the invention, 90° side scatter measurements may be made with a fluorescence photometer, e.g., a CARY ECLIPSE instrument (Varian, Inc. Palo Alto, Calif., USA). Liquid samples are usually analyzed in standard quartz cuvettes. The wavelength of the incoming light may be 800 nm; 90° side scatter may be measured at the same wavelength (i.e. 800 nm). The parameter settings of the instrument may be following:

Instrument: Cary Eclipse
Instrument serial numberEL06033429
Data Mode Fluorescence
Em.Wavelength (nm)800
Ex. Wavelength (nm)800
Ex. Slit (nm)5
Em. Slit (nm)5
Ave Time (sec) 0.1
Excitation filter Auto
Emission filter open
PMT voltage (V) medium
Multicell holder Multicell
Multi zero Off
Replicates 1
Sample averaging off For the purpose of the present invention, a "clear" aqueous composition is characterized by a turbidity (determined as above) which is about equivalent to (i.e. about equals) the turbidity of a solution without protein with enzymatic activity of alpha-galactosidase but otherwise with the same composition and concentrations of the respective ingredients. Preferably, this corresponds to the range of from 0 to 0.40, more preferably from 0 to 0.13, still more preferred to the range of 0.05 and 0.130, determined as 90° side scatter using light with a wavelength of 800 nm under the conditions described.

In the context of the present invention, a "protein with enzymatic activity of alpha-galactosidase" generally refers to any kind of protein revealing alpha-galactosidase activity. The alpha-galactosidase activity of the present invention is characterized by the hydrolysis of galactosidase residues, in particular by the hydrolysis of terminal alpha-D-galactose residues in alpha-D-galactosides, including galactose oligosaccharides and galactomannans. More in particular, the alpha-galactosidase activity of the present invention refers to the hydrolysis of terminal 1,3-linked galactosidase residues. Assays for the analysis of alpha-galactosidase enzymatic activity are well established in the art and are described, e.g., in detail by Liu et al. (2007). Such enzymatic assays can be carried out in an in vitro set up, and aim at determining the enzymatic activity of a protein by analyzing the catalytic cleavage of a synthetic substrate, e.g., a monosaccharide Gal$\alpha$-pNP or a B tetrasaccharide-AMC substrate. One unit of enzyme activity is thereby defined as the amount of enzyme required to cleave 1 µmole of substrate per minute in the presence of a certain amount of substrate in a defined volume. The enzymatic activity is then calculated by determining the specific activity based on complete cleavage of the substrate in the reaction volume. In case of the Gal$\alpha$-pNP substrate, for example, the formation of p-Nitro-Phenol (pNP) is quantified at a wavelength of 405 nm. A test for analyzing the enzymatic activity of alpha-galactosidase according to the present invention is, for example, described in Example 1.

The term "arginine" as used herein denotes the $\alpha$-amino acid arginine (also abbreviated as Arg or R), preferably L-arginine or D-arginine, or a mixture thereof, especially L-arginine. Arginine is one of the 20 most commonly found amino acids in nature. An $\alpha$-amino acid consists of a central carbon atom, termed the $\alpha$-carbon, linked to an amino group, a carboxylic acid group, a hydrogen atom, and a distinctive R group, often referred to as the side chain. Arginine consists of a 4-carbon aliphatic side chain, the distal end of which is capped by a guanidinium group. With a pKa value of 12.48, the guanidinium group is positively charged in neutral, acidic and even most basic environments, and thus impairs basic chemical properties to the molecule. On DNA level, arginine is encoded by the codons CGU, CGC, CGA, CGG, AGA, and AGG, respectively. The term "arginine" also includes the amino acid in any of its salt forms.

As demonstrated within the context of the present invention, a composition comprising a protein with enzymatic activity of alpha-galactosidase is stabilized in the presence of arginine at a concentration of above 100 mM, in particular at a concentration of at least 150 mM and higher. These concentrations include any concentrations. From experiments with other proteins it is concluded that the concentration of arginine can be increased up to 2 M without affecting the structure and/or the function of the protein.

Accordingly, in a preferred embodiment, the composition of the present invention comprises arginine at a concentration of between 150 mM and 2 M. Molarity (in units of mol/L, molar, or M) or molar concentration denotes the number of moles of a given substance per liter of solution. A capital letter M is used to abbreviate the units of mol/L.

As stated above, the concentration of arginine is more than 100 mM including concentrations of arginine of at least, e.g., 110 mM, 120 mM, 130 mM, 140 mM, 150 mM, 200 mM, 220 mM, 250 mM, 275 mM, 300 mM, 320 mM, 350 mM, 375 mM, 400 mM, 425 mM, 450 mM, 475 mM, or 500 mM, preferably at least 110, mM, 120 mM, 130 mM, 140 mM, 150 mM, 200 mM, 220 mM, or 250 mM, especially at least 150 mM, 200 mM, 220 mM or 250 mM.

As stated above, the concentration of arginine can be increased up to 2 M including concentrations of arginine of at most, e.g., 200 mM, 220 mM, 250 mM, 275 mM, 300 mM, 320 mM, 350 mM, 375 mM, 400 mM, 425 mM, 450 mM, 475 mM, 500 mM, 550 mM, 600 mM, 650 mM, 700 mM, 750 mM, 800 mM, 850 mM, 900 mM, 1 M, or 1.5 M, preferably at most 400 mM, 320 mM or 200 mM, especially at most 320 mM.

In another preferred embodiment, the composition according to the present invention comprises arginine at a concentration of between 200 and 400 mM.

In the context of the present invention, it has been demonstrated that the composition comprising a protein with enzymatic activity of alpha-galactosidase is stabilized in the presence of arginine at a concentration of between 250 mM and 320 mM, in particular in the presence of 310 mM arginine.

Accordingly, in another more preferred embodiment, the composition of the present invention comprises arginine at a concentration of between 250 mM and 320 mM, most preferably at a concentration of about 310 mM. The term "about" as used in the context of the present invention means the indicated value±10%, preferably ±5%, especially ±4%, 3%, 2% or 1%.

An aqueous solution containing ions conducts electricity. Consequently, measuring the conductance of a solution can be a suitable tool to investigate whether the solution contains dissociated ions, and whether any chemical reactions in the solution are producing or consuming ions. Any solution, even one containing ions, however, provides considerable resistance to the flow of current through it. Conductivity is the reciprocal of said resistance. That is, high resistance means low conductivity, and low resistance means high conductivity. It is a standard method in the art to measure the conductivity of a solution by using the solution to complete an electrical circuit, usually by inserting a pair of electrodes into the circuit, and immersing the electrodes in the solution. A conductivity sensor measures how much electricity is being conducted through a centimeter of water. Specific conductivity is expressed as mhos per centimeter (M/cm), also called siemens per centimeter (S/cm). Because a mho (or siemens) is a very large unit, the micromho (microsiemens) or millimho (millisiemens) typically is used (mS/cm). Since conductivity varies with temperature, it is necessary to correct the readings for changes in temperature. Most instruments contain circuits that automatically compensate for temperature and correct the readings to a standard 25° C. Suitable methods of measuring conductivity under standard conditions are known to the skilled person, and one of these is exemplified in Example 3.

As detailed above, the composition of the present invention can comprise; in addition to arginine, any sort of salt ions, buffer ingredients and/or chemical agent suitable to establish a favourable environment for the protein of interest. In the context of the present invention, it was found that a protein with alpha-galactosidase activity is stabilized in the presence of arginine and in the absence of high salt concentrations, i.e. under low salt conditions. Such low salt conditions include, but are not limited to, a concentration of mono-, di- or trivalent salt ions of at most 0.5 M, more preferably of at most 450 mM, 400 mM, 350 mM, 300 mM, 250 mM, 200 mM, 150 mM, 100 mM, 50 mM, 25 mM or 10 mM, especially of at most 50 mM. It is noted that the above concentration values are intended not to include the arginine present in the composition.

In a preferred embodiment, the composition of the present invention comprises arginine at a concentration of about 310 mM, and mono-, di- or trivalent salt ions at a final concentration of at most 50 mM. In another preferred embodiment, the composition of the present invention comprises mono-, di- or trivalent salt ions at a final concentration of at most 350 mM. Said mono-, di- or trivalent salt ions may include, but are not limited to, $Na^+$, $K^+$, $Mg^{++}$, $PO_4^{3-}$, $Ca^{++}$, $Cl^-$, and alike.

Accordingly, corresponding to the exact salt concentration used, the conductivity of the composition of the present invention is between 5 mS/cm and 50 mS/cm.

In a preferred embodiment, the conductivity of the composition of the present invention is at most 40 mS/cm. In yet another preferred embodiment, the composition of the present invention has a conductivity of between 15 mS/cm and 25 mS/cm, more preferably between 18 mS/cm and 22 mS/cm.

The term "mS/cm" as used herein refers to the unit of conductivity in milisiemens per cm of solution, with S referring to the official Systeme Internationale (SI) name of the unit. As detailed above, the conductivity of an aqueous solution can be measured by means of standard methods known to a person skilled in the art. Devices for measuring conductivity are commercially available, and can be purchased from several suppliers, including, e.g., Sartorius (Gottingen, Germany). In the context of the present invention, the term "mS/cm" is defined to include a deviation of +/−0.1 mS/cm. The conductivity of the composition according to the present invention is, e.g., exemplified in Table 2 of the present application (see Example 3).

As described above, stabilization of the alpha-galactosidase enzyme in solution also depends on the pH value of the composition containing the protein. That is, recombinant alpha-galactosidase, in particular alpha-galactosidase derived from *Bacteriodes fragilis*, is unstable in buffers with alkaline pH values (i.e. pH values of ≧9.0), resulting in an irreversible loss of enzyme activity. As demonstrated in the context of the present invention (see, e.g., Example 3), the alpha-galactosidase of the present invention remained in solution at alkaline pH values (i.e. at a pH value of 9.0 and 9.5).

Accordingly, in a preferred embodiment, the composition of the present invention has a pH of between pH 5 and pH 7.5. In another preferred embodiment, the composition of the present invention has a pH of between pH 5.5 and pH 7, more preferably of between pH 5.8 and pH 6.5.

The term "pH" as used herein refers to the concentration of $H^+$ ions in solution, and is defined as $pH=\log 10\ (1[H^+])=-\log 10\ [H^+]$. The analysis of the pH value of a composition according to the present invention is a standard method and well known to the person skilled in the art. Devices for measuring the pH in solution are commercially available from diverse suppliers, including, e.g., Mettler-Toledo (Giessen, Germany). It is noted that the term "pH" as used in the context of the present invention is defined to include a deviation of +/−0.2 pH values.

As detailed above, a particular DNA encoding a protein of interest can be introduced into a suitable host cell(s) to produce the respective protein by recombinant means. These host cells can by any kind of suitable cells, preferably bacterial or eukaryotic cells, e.g., grown in culture. At a first step, this approach may include the cloning of the respective gene into a suitable plasmid vector. Plasmid vectors are widely used for gene cloning, and can be easily introduced, i.e. transfected, into bacterial cells which have been made transiently permeable to DNA. After the protein has been expressed in the respective host cell, the cells can be harvested and serve as the starting material for the preparation of a cell extract containing the protein of interest. A cell extract containing the protein of interest is obtained by lysis of the cells. Methods of preparing a cell extract by means of either chemical or mechanical cell lysis are well known to the person skilled in the art, and include, but are not limited to, e.g., hypotonic salt treatment, homogenization, douncing or ultrasonification.

In the context of the present invention, it has been demonstrated that a composition comprising a protein with alpha-galactosidase activity derived from a bacterial host cell is stabilized in the presence of arginine at a concentration of above 100 mM, in particular at a concentration of at least 150 mM. A composition comprising a protein with alpha-galactosidase activity derived from a bacterial host cell is intended to refer to any kind of lysate of the host cell, optionally after having been processed, e.g., by centrifugation, chromatography, dialysis, or ultrafiltration as described below.

Accordingly, in a preferred embodiment, the composition of the present invention is derived from a bacterial host cell. In a further preferred embodiment, the composition of the present invention is derived from the bacterial strain *Escherichia coli* (*E. coli*).

The term "bacterial host cell" as used herein refers to any kind of bacterial organism suitable for application in recombinant DNA technology, and includes all known bacterial strains, in particular those which can be used as host cells for expressing one or more recombinant protein(s). The bacterial stain *Escherichia coli* (*E. coli*) is well characterized and represents the mostly used expression system for the rapid and economic production of recombinant proteins. A variety of *E. coli* bacterial host cells are known to a person skilled in the art and include, but are not limited to, strains such as DH5-alpha, HB101; MV1190, JM109, JM101, or XL-1 blue which can be commercially purchased from diverse suppliers including, e.g., Stratagene (CA, USA), Promega (WI, USA) or Qiagen (Hilden, Germany). A suitable host cell and a composition according to the present invention derived from *E. coli* is, e.g., exemplified in Example 5 of the present invention.

In the context of the present invention, it has been found that the protein concentration of the composition according to the present invention is typically in the range of 20-30 mg/ml (see, e.g., Example 5).

Accordingly, in a preferred embodiment, the composition of the present invention has a protein concentration of at least 20 mg/ml.

The term "protein concentration" as used herein generally refers to the total protein content of the composition according to the present invention calculated per volume (e.g., mg/ml). This definition may include any reference to a protein concentration of a total cell extract derived from either a prokaryotic or eukaryotic cell and containing the protein of the present invention, or may equally refer to the protein concentration of a composition comprising the protein of the present invention in either partially or substantially purified form. Accordingly, the protein concentration as referred to herein may relate to any protein content which is measured at any step during or after the method of providing alpha-galactosidase according to the present invention. Methods for determining protein concentrations of a particular composition are well known to the person skilled in the art, and include, e.g., the use of a Bradford assay; or by simply measuring the absorbance of a protein solution at 280 nm.

Concentrating a protein in composition can be carried out by diverse standard methods including, e.g., the use of ultra centrifugal filter devices. Such filter devices provide high recoveries (typically >95%) of even dilute (ng to μg/mL) protein solutions, and employ filter membranes with cut-offs available in the range of 3,000, 10,000, 30,000, 50,000 to 100,000 NMWL (Nominal Molecular Weight Limit). Ultra centrifugal filter devices can be commercially purchased from different suppliers, e.g., from Millipore (MA, USA).

In the context of the present invention, the enzymatic activity of the alpha-galactosidase has further been determined by biochemical means. As demonstrated by the Examples (see, e.g., Example 1), the protein of the present invention generally reveals an enzymatic activity of alpha-galactosidase of 0.5 to 0.8 units/mg, with respect to the total protein content of the composition.

Accordingly, in a preferred embodiment, the composition of the present invention is characterized in that the enzymatic activity of alpha-galactosidase is between 0.5 and 0.8 units/mg of total protein.

As detailed above, assays for determining enzymatic activity of alpha-galactosidase are well established in the art and are described, e.g., in detail by Liu et al. (2007). These assays employ cleavage of artifical substrates, e.g., the monosaccharide Galα-pNP or the B tetrasaccharide-AMC substrate. One unit of enzyme activity is thereby defined as the amount of enzyme required to cleave 1 μmole of substrate per minute using a defined reaction volume in the presence of a defined amount of substrate. The enzymatic activity is then calculated by determining the specific activity based on complete cleavage of the substrate in the reaction volume. The enzyme activity may be measured as exemplified in Example 1.

The term "units/mg" as defined herein generally refers to the units of enzyme activity per 1 mg of total protein content in mg as determined by biochemical means, as also described above. Said total protein content may be derived from a whole cell extract containing the enzymatic activity of the present invention, or may be derived from a purified composition comprising a protein with alpha-galactosidase activity.

In a preferred embodiment, the protein of the present has a substrate specificity of EC 3.2.1.22. In another preferred embodiment, the composition of the present invention comprises a protein which hydrolyses terminal alpha-1,3-galactosyl moieties.

As detailed above, the term "EC 3.2.1.22" refers to the systematic number which has been assigned to the enzyme class of alpha-galactosidase by the Enzyme Commission of the International Union of Biochemistry in accordance with the type of the enzymatic reactivity of the enzyme. In particular, the systematic number EC 3.2.1.22 specifies the catalytic mechanism of alpha-galactosidases as the hydrolysis of terminal alpha-D-galactose residues in alpha-D-galactosides. In the context of the present invention, the catalytic mechanism of alpha-galactosidase particularly refers to the hydrolysis of terminal alpha-1,3-galactosidase residues as, e.g., found on group B red blood cells, constituting the blood group B antigens.

Alpha-galactosidases are found in a wide variety of organisms.

Accordingly, in a preferred embodiment, the composition of the present invention comprises a protein with enzymatic activity of alpha-galactosidase characterized in that said protein is a naturally occurring protein. Alternatively, the protein of the invention is a functionally active fragment or derivative of said naturally occurring protein.

In yet another preferred embodiment, the protein of the present invention is derived from an organism selected from the group consisting of human, animal, plant, fungi and bacteria.

A "naturally occurring protein" as referred to in the context of the present invention generally denotes a protein which is naturally found in any kind of living organism, and which can as such be isolated from tissues, liquids, and/or from any sort of individual cells of said organism. Moreover, said naturally occurring protein might further be isolated from the organism as a whole, e.g., by providing a whole cell extract of the organism comprising said protein. The organisms from which said naturally occurring protein might originate include, but are not limited to, human, animal (including insects), plant such as coffee plant, fungi (including yeast), and bacteria such as *Pseudoalteromonas* spec. or *Bacteroides* sp.

The term "a functionally active fragment or derivative" as used herein refers to any kind of protein revealing enzymatic activity of alpha-galactosidase that comprises the amino acid sequence of a naturally occurring protein with alpha-galactosidase activity in any partially, substituted or modified form.

That is, a functionally active fragment of the present invention might be comprised of protein domain(s) originated from a naturally occurring protein with alpha-galactosidase activity revealing the same enzymatic activity as the wild type protein it derived from. Such a functionally active fragment might be constituted of any N-terminal, C-terminal or central protein domain of interest, or of any combination of the latter.

Furthermore, a functionally active derivative might also comprise additional amino acid as compared to the wild-type sequence which might be present, e.g., as part of N- or C-terminal extensions and/or as part of inner protein domains.

The functionally active fragment may be further characterized by structural features. Accordingly, in one preferred embodiment of the invention the functionally active fragment consists of at least 60%, preferably at least 70%, more preferably at least 80%, still more preferably at least 90%, even more preferably at least 95%, most preferably 99% of a naturally occurring protein with enzymatic activity of alpha-galactosidase such as, e.g., alpha-galactosidase from *Bacteroides fragilis* (strain ATCC 25285 (American Type Culture Collection, Manassas, Va. USA), also designated NCTC 9343 (National Collection of Type Cultures, London, UK)). One example of such a fragment is the protein as shown in SEQ ID NO: 1. The functionally active fragment as defined above may be derived from the protein by one or more amino acid deletions. The deletions may be C-terminally, N-terminally and/or internally.

The percentage of sequence identity can be determined, e.g., by sequence alignment. Methods of alignment of sequences for comparison are well known in the art. Various programs and alignment algorithms have been described in, e.g., Smith and Waterman (1981) or Pearson and Lipman (1988).

The NCBI Basic Local Alignment Search Tool (BLAST) (Altschul et al., 1990) is available from several sources, including the National Center for Biotechnology Information (NCBI, Bethesda, Md.) and the Internet, for use in connection with the sequence analysis programs blastp, blastn, blastx, tblastn and tblastx.

The functionally active derivative of protein with enzymatic activity of alpha-galactosidase is obtain by sequence alterations in the protein (one or more amino acid deletions, substitutions and/or additions), wherein the protein with the sequence alterations retains a function of the unaltered protein, namely its ability to hydrolyze the terminal alpha-galactosyl moieties from glycolipids and glycoproteins. Such sequence alterations can include, but are not limited to, conservative substitutions, deletions, mutations and insertions. However, the functionally active derivative exhibits enzymatic activity of alpha-galactosidase. This characteristic of the functionally active fragment or derivative can be assessed, e.g., as detailed in Example 1.

Moreover, a functionally active derivative of the present invention might comprise one or more modified amino acids including, but not limited to, e.g., phosphorylated, acetylated, ubiquitinated, and/or sumolylated residues. A functionally active derivative of the present invention might further encompass any sort of chemical label such as, e.g., fluorescence-labeled moieties. As detailed above, a functionally active fragment or derivative of a naturally occurring alpha-galactosidase can be identified and biochemically characterized by means of standard assay in which the enzymatic activity of a protein is determined by visualizing the cleavage of artificial substrates. Such assays are well known in the art and are described, e.g., in Liu et al. (2007).

The term "functionally active derivative" includes naturally-occurring allelic variants, as well as mutants or any other non-naturally occurring variants. As is known in the art, an allelic variant is an alternate form of a (poly)peptide that is characterized as having a substitution, deletion, or addition of one or more amino acids that does essentially not alter the biological function of the polypeptide. By "biological function" is meant a function of the polypeptide in the cells in which it naturally occurs, even if the function is not necessary for the growth or survival of the cells. For example, the biological function of a porin is to allow the entry into cells of compounds present in the extracellular medium. The biological function is distinct from the antigenic function. A polypeptide can have more than one biological function.

In the context of the present invention a functionally active fragment or derivative has enzymatic activity of alpha-galactosidase, if the activity of the fragment or derivative amounts to at least 10%, preferably at least 25%, more preferably at least 50%, even more preferably at least 70%, still more preferably at least 80%, especially at least 90%, particularly at least 95%, most preferably at least 99% of the activity of the protein without sequence alterations.

In a preferred embodiment, the functionally active derivative or fragment derived from the naturally occurring protein by amino acid exchanges, deletions or insertions may also conserve, or more preferably improve, the enzymatic activity.

In a still more preferred embodiment of the invention the functionally active derivative of the naturally occurring protein with enzymatic activity of alpha-galactosidase has at least 50% sequence identity to the protein, especially at least 60%, preferably at least 70%, more preferably at least 80%, still more preferably at least 90%, even more preferably at least 95%, most preferably 99% to the protein and is preferably derived from the protein by conservative substitutions. Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side Chains, with small side chains, with large side chains etc. In one embodiment, one conservative substitution is included in the peptide. In another embodiment, two conservative substitutions or less are included in the a further embodiment, three conservative substitutions or less are included in the peptide.

Examples of conservative amino acid substitutions include, but are not limited to, those listed below:
Original Residue Conservative Substitutions
  Ala Ser
  Arg Lys
  AsnGln; H is
  Asp Glu
  Cys Ser
  Gln Asn
  Glu.Asp
  His Asn; Gln
  Ile Leu, Val
  Leu Ile; Val
  Lys Arg; Gln; Asn
  Met Leu; Ile
  Phe Met; Leu; Tyr
  Ser Thr
  Thr Ser
  Trp Tyr
  Tyr Trp; Phe
  Val Ile; Leu The protein of the invention may further be fused to an epitope tag which provides an epitope to which an anti-tag substance can selectively bind. The epitope tag is generally placed at the amino- or carboxyl-terminus of the peptide but may be incorporated as an internal insertion or substitution as the biological activity permits. The presence of such epitope-tagged forms of a peptide can be detected using a substance such as an antibody against the tagged peptide. Also, provision of the epitope tag enables the peptide to be readily purified by affinity purification using an anti-tag antibody or another type of affinity matrix that binds to the epitope tag. Various tag polypeptides and their respective antibodies are well known in the art. Examples include poly-histidine (poly-his), poly-histidine-glycine (poly-his-gly) tags, the HA tag polypeptide, the c-myc tag, the Strep tag and the FLAG tag.

The term "bacteria" as referred to in the context of the present invention might include all variants of microbial cells, example of which may include, but are not limited to, obligate anaerobic Gram-negative microorganism, preferably a microorganism from the genus *Bacteroides*, such as *Bacteroides caccae, Bacteroides distasonis, Bacteroides eggerthii, Bacteroides fragilis, Bacteroides merdae, Bacteroides ovatus, Bacteroides stercoris, Bacteroides thetaiotaomicron, Bacteroides uniformis*, and *Bacteriodes vulgatus*.

In a preferred embodiment, the composition of the present invention comprises a protein with alpha-galactosidase activity derived from the bacterial organism *Bacteroides fragilis*, more preferably any naturally occurring form of *Bacteroides fragilis* alpha-galactosidase.

In the context of the present invention, a protein with alpha-galactosidase activity derived from *Bacteroides fragilis* might be either of the two alpha-galactosidase homologs found in *B. fragilis*. The two homologs, namely alpha-galactosidase A and alpha-galactosidase B, are encoded by the genes galA and galB, respectively. The enzymes are constituted by 605 and 595 amino acids each. A protein with alpha-galactosidase activity derived from *Bacteroides fragilis* removes both branched alpha-1,3-linked galactose residues of blood group B antigens and linear alpha-1,3-linked galactose structures. The catalytic activity of said proteins includes the hydrolys is of terminal, non-reducing linear alpha-1,3-linked galactose residues, the hydrolysis of terminal, non-reducing branched alpha-1,3-linked galactose residues, as well as the hydrolysis of terminal, non-reducing alpha-D-galactose residues in alpha-D-galactosides, including galactose oligosaccharides, galactomannans and galactohydrolase.

In another preferred embodiment, the composition of present invention comprises a fragment of alpha-galactosidase derived from *Bacteroides fragiles* comprising or consisting of the amino acid sequence of SEQ ID NO: 1. In yet another preferred embodiment, the composition comprises any functionally active derivative or fragment thereof.

Figure 3:
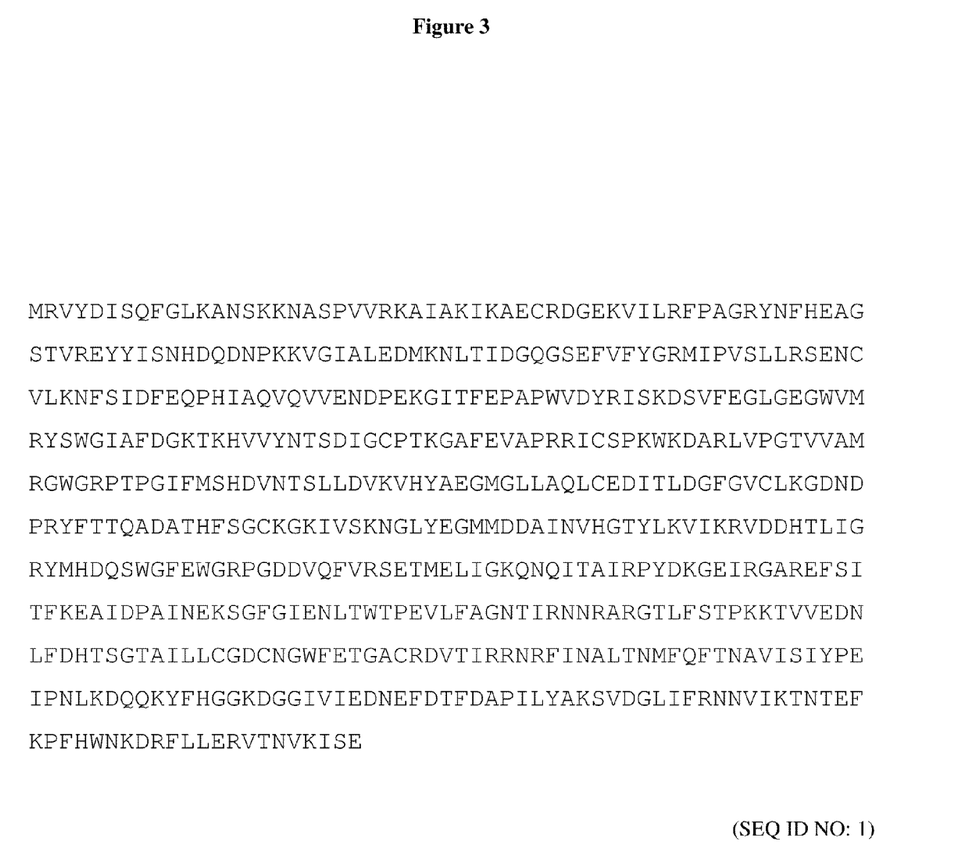
FIG. 3 shows the amino acid sequence (SEQ ID NO: 1) of an apha-galactosidase fragment (fragA) from the organism *Bacteroides fragilis* with a total length of 572 amino acids (aa). The protein has a calculated molecular weight of 64564.8 Da, and a calculated isoelectric point of 6.72.

The term "SEQ ID NO: 1" as referred to herein denotes the amino acid sequence as shown in SEQ ID NO: 1 (also depicted in FIG. 3), and represents the amino acid sequence of alpha-galactosidase as found in *B. fragiles* NCTC (National Collection of Type Cultures, London, UK) 9343 (strain ATCC 25285. (American Type Culture Collection, Manassas, Va. USA), also designated fragA). The amino acid sequence of SEQ ID NO: 1 is identified by the EMBL (European Molecular Biology Laboratory, Heidelberg, Germany) Nucleotide Sequence Database Accession No. AM109955.

In this context, the term "a functionally active derivative or fragment thereof" generally refers to the definition as detailed above. In particular, said refers to any kind of fragment or derivative comprising or consisting of amino acids of SEQ ID NO: 1, including, but not limited to, every smaller fragment revealing enzymatic activity of alpha-galactosidase, or any fragment comprising additional amino acids, as defined above for the fragments and derivates of naturally occurring proteins with alpha-galactosidase activity. Said additional amino acids can either be present at the N-terminus, the C-terminus or be part of inner domains of the protein. Said additional amino acids may further comprise, but not limited to, affinity purification tags including, e.g., the 6×His- (SEQ ID NO: 2), GST-, NusA-, NusB-, or Protein A-tag. Such affinity tags are commonly known to a person skilled in the art and are routinely used in the context of recombinant protein expression. Moreover, a functionally active derivative or fragment of SEQ ID NO: 1 includes any protein consisting or comprising the amino acids as shown in SEQ ID NO: 1 or part of it which comprises one or more modified amino acid(s) or any kind of other chemical modification(s). As further detailed above, the enzymatic activity of a functionally active derivative or fragment can be determined by standard methods known to a person skilled in the art (see, e.g., Liu et al., 2007).

Preferably, the composition of the invention may be characterized in, that it comprises
  (i) a naturally occurring protein with enzymatic activity of alpha-galactosidase, preferably a protein with enzymatic activity of alpha-galactosidase according to SEQ ID NO: 1, and
  (ii) arginine at a concentration of between 250 mM and 320 mM, and in that it has
  (iii) a conductivity of 20 mS/cm±0.1 mS.

In another preferred embodiment, the composition of the invention may be characterized in that it comprises (i) a naturally occurring protein with enzymatic activity of alpha-galactosidase, preferably a protein with enzymatic activity of alpha-galactosidase according to SEQ ID NO: 1, and (ii) arginine at a concentration of between 250 mM to 320 mM, and in that it has (iii) a pH of 5.8 to 6.2.

More preferably, the composition of the invention may be characterized in that it comprises (i) a naturally occurring protein with enzymatic activity of alpha-galactosidase, preferably a protein with enzymatic activity of alpha-galactosidase according to SEQ ID NO: 1, and (ii) arginine at a concentration of between 250 mM, to 320 mM, and in that it has (iii) a conductivity of 20 mS/cm±0.1 mS, and (iv) a pH of 5.8 to 6.2.

Most preferably, the composition of the invention may be characterized in that it comprises (i) a naturally occurring protein with enzymatic activity of alpha-galactosidase, preferably a protein with enzymatic activity of alpha-galactosidase according to SEQ ID NO: 1, and (ii) arginine at a concentration of between 250 mM to 320 mM, preferably at a concentration of 310 mM, and (iii) mono-, di-, or trivalent salt ions at a concentration of at most 50 mM, and in that it has (iv) a conductivity of 20 mS/cm f 0.1 mS, and (v) a pH of 5.8 to 6.2.

With respect to the above described embodiments, it is equally preferred that the composition of the present invention comprises a functionally active fragment or derivative of a naturally occurring protein with enzymatic activity of alpha-galactosidase, or a functionally active fragment or derivative of a protein according to SEQ ID NO: 1.

In the context of the present invention, it has further been demonstrated that the addition of arginine to a protein composition results in the stabilisation of alpha-galactosidase.

Accordingly, in a further aspect, the present invention provides a method of stabilizing an aqueous composition comprising a protein with enzymatic activity of alpha-galactosidase, characterized in, that said method comprises the step of adding arginine to said composition to a final concentration of above 100 mM, in particular of at least 150 mM.

In this context, the terms "aqueous composition", "a protein with enzymatic activity of alpha-galactosidase", "arginine" and "concentration" are to be understood as detailed above.

The term "stabilizing" or "stabilization" as used in the context of the present invention includes any kind of process which facilitates and/or enables a protein of interest to be stable or to keep in solution, including any process which facilitates and/or enables the solubilisation of a protein of interest at any temperature, e.g., of in between 4° C. and 37° C. The solubilisation and/or stabilization of a protein includes, but is not limited to, the absence of appearance of precipitation and/or aggregation product(s), the presence and/or absence of which can be analysed by standard methods known in the art including, e.g., the analysis by means of visual inspection, by means of optical density measurements including, e.g., the determination of the total protein content of a respective composition containing the stabilized protein, and/or by means of protein analysis using standard biochemical techniques (e.g., SDS-polyacrylamid gel electrophoresis). The term "stabilizing" or "stabilization" further includes the feasibility of a protein to catalyze an enzymatic reaction. In particular, in the context of the present invention, a stabilized protein according to the method of the present invention reveals enzymatic activity of alpha-galactosidase, more in particular, the hydrolysis of 1,3-linked galactosidase residues. As already described above, said enzymatic activity can be determined and evaluated by means of biochemical standard assays known to the person skilled in the art (see, e.g., Liu et al., 2007). Moreover, stabilization of a protein according to the present invention also includes the feasibility to concentrate a protein of interest in solution up to a concentration of at least 20 mg/ml without loss of the protein due to precipitation and/or aggregation.

In a preferred embodiment, said stabilized composition is characterized as in any of the embodiments detailed above in the context of the aqueous composition of the present invention.

In the context of the present invention, it has further been demonstrated that a protein with enzymatic activity of alpha-galactosidase can be purified by means of ion-exchange chromatography, in particular by the use of cation exchange chromatography, when stabilized in the presence of arginine at a concentration of above 100 mM, preferably at a concentration of at least 150 mM. The application of cation exchange chromatography in the context of the present invention has only been made possible by stabilizing the protein according to the present invention.

Accordingly, in a further aspect, the present invention provides a method of preparing a purified aqueous composition comprising a protein with enzymatic activity of alpha-galactosidase, said method comprising the steps of (a) providing a composition containing said protein with enzymatic activity of alpha-galactosidase, (b) concentrating the composition of step (a) in the presence of arginine at a concentration of above 100 mM, in particular of at least 150 mM, and (c) purifying the composition of step (b) via cation exchange chromatography.

In this context, the terms "aqueous composition", "a protein with enzymatic activity of alpha-galactosidase", "arginine" and "concentration" are to be understood as detailed above.

The term "providing a composition" as used in the context of the present invention refers to all sorts of procedures suitable to prepare a composition containing a protein of interest. These procedures include, but are not limited to, the preparation of whole cell extracts derived from any kind of organism containing the protein of interest, the preparation of total cell extracts from particular species of cells, e.g., grown in culture, and containing the protein of interest, including, but not limited to, the preparation of total cell extracts derived from a bacterial host cell expressing a recombinant protein of interest, or the preparation of a protein composition by any other means. As detailed above, the preparation of a cell extract may include all necessary steps of harvesting a cell from a culture by means of; e.g., diverse centrifugation and/or fractionation steps, or the steps of lysing the cells by either mechanical or chemical means including, but not limited to, e.g., multiple freezing and/or thawing cycles and/or ultrasonic treatment of the cells.

Preferably, said composition is an aqueous composition. The term "aqueous composition" is to be understood as detailed above.

The term "concentrating the composition" as used herein refers to any enhancement with respect to a given protein concentration of a composition and/or a solution. Such enhancement can be achieved by means of biochemical standard methods. Such methods are well known to the person skilled in the art, and include, e.g., dialysis and/or ultrafiltration (i.e. diafiltration) by the use of ultra centrifugal filter devices. As detailed above, such filter devices employ filter membranes with cut-offs available in the range of 3.000, 10.000, 30.000, 50.000 to 100.000 NMWL (Nominal Molecular Weight Limit), and can be commercially purchases from different suppliers, e.g., from Millipore (MA, USA).

In general, proteins can be purified on the basis of their characteristics such as solubility, size, charge, and specific binding affinity. That is, proteins are often separated on the basis of their net charge by ion-exchange chromatography.

The term "cation exchange chromatography" as used in the context of the present invention generally refers to all kind of procedures in which positively charged proteins (i.e. cationic proteins having a net positive charge at neutral pH such as the protein of the present invention) can be bound to negatively charged resins containing carboxylate groups such as carboxymethyl-cellulose (CM-cellulose) or carboxymethyl-agarose (CM-agarose). A positively charged protein bound to such a resin can then be eluted by increasing the concentration of sodium chloride or of another salt in the elution buffer since the sodium ions compete with positively charged groups on the protein surface for binding to the column. By means of cation exchange chromatography, the person skilled in the art is able to separate a protein of interest from other proteins by binding to a particular resin, the procedure of which includes washing of the bound protein and eluting of the protein in the presence of increasing salt concentrations. Therefore, the cation exchange chromatography according to the present invention enables the person skilled in the art to purify a protein with enzymatic activity of alpha-galactosidase in its native state to high yields by biochemical means. The cation exchange chromatography according to the present invention is, e.g., exemplified in Example 6 of the present invention.

In a preferred embodiment, the composition of step (b) is defined as in any of the embodiments described above.

Usually, protein mixtures are subjected to a series of separation steps, each based on a different property to yield a pure protein.

Accordingly, in another preferred embodiment, the method of the present invention comprises one or more additional purification step(s) (i) before and/or after step (b), and/or (ii) before and/or after step (c).

The term "additional purification step(s)" as used herein refers to any kind of biochemical method which supports and/or enables the purification of a protein of interest. Such standard methods are well known to a person skilled in the art, and include e.g., salting out, dialysis, (ultra)filtration, (ultra) centrifugation, gel-filtration chromatography, anion-exchange chromatography, and/or affinity chromatography.

In detail, salting out is based on the effect that most proteins are less soluble, e.g., at high salt concentrations. The salt concentration at which a protein precipitates differs from one protein to another. Accordingly, salting out can be used to fractionate and thus separate proteins from each other, for example by the use of ammonium sulfate. Salting out is also useful for concentrating dilute solutions of proteins, including active fractions obtained from other purification steps.

Dialysis can be used to separate proteins from, e.g., small molecules by means of a semipermeable membrane, for example a cellulose membrane including pores of a defined size. Molecules having dimensions greater than the pore diameter are retained inside the dialysis bag, whereas smaller molecules and ions traverse the pores of such a membrane.

(Ultra)filtration can be used to, e.g., further separate the protein from other components of the composition. Filter materials which may be used are cellulose nitrate, cellulose acetate, PVC, Teflon or ceramic membranes, for example made of zirconium oxide. The filters may be individual membranes or assembled in membrane systems, such as, for example, modules. The modules may be tubular modules, spiral modules or wound modules or hollow fibre modules. The filters may have a pore size of up to approximately 5 μm, preferably 4 μm, more preferably 3 μm and most preferably 1 μm. The pore size of filter used for ultrafiltration is preferably no more than 100 000 NMGT (Nominal Molecular Weight Limit), more preferably no more than 75 000 NMGT, still more preferably no more than 50 000 NMGT and most preferably no more than 30 000 NMGT. The pore size of the filters used for sterile filtration is preferably no more than 0.8 μm, more preferably no more than 0.6 μm, still more preferably no more than 0.4 μm and most preferably no more than 0.22 p.m. Filter devices used for filtration or ultrafiltration are commercially available from diverse suppliers including, e.g., Sartorius (Gottingen, Germany) or Millipore (MA, USA).

Gel-Filtration chromatography can be used to achieve a separation of proteins on the basis of their sizes. The protein is applied on the top of a column consisting of a porous beads made of an insoluble but highly hydrated polymer such as dextran, agarose or polyacrylamide. Commonly used commercial preparation of these beads include, but are not limited to, Sephadex, Sepharose, and Biogel, and are typically 100 μm in diameter.

Anion-exchange chromatography can be used to separate negatively charged proteins (anionic proteins) by binding of the proteins to positively charged diethylaminoethyl-cellulose (DEAE-cellulose) resins and/or membranes. An example of anion-exchange chromatography suitable to provide a purified composition according to the present invention is, e.g., detailed in Example 6.

Affinity chromatography is a technique which takes advantages of the high affinity of many proteins for specific chemical groups, and can be effectively used to isolate a protein that recognizes a particular group by (1) covalently attaching said group or a derivative thereof to a column, and (2) adding a mixture of proteins to this column, which is then washed with buffer to remove unbound proteins, and (3) eluting the desired protein by adding a high concentration of a soluble form of said group or altering the conditions to decrease binding affinity. In general, affinity chromatography is most effective when the interaction of the protein and the molecule which is used as the bait is highly specific.

Furthermore, at each step of the method(s) according to the present invention, the composition of the present invention might be further analyzed, e.g., in order to determine its precise protein concentration before further processing of the sample is carried out.

In a preferred embodiment of the present invention, a composition of the invention is essentially prepared as described in Example 5. That is, alpha-galactosidase (e.g., B-zyme or the protein of SEQ ID NO: 1) is expressed or over-expressed in a suitable host cell, e.g., *E. coli* HB101. The host cells are lysed (e.g., by thawing and/or by means of an APV high pressure device) and the protein is isolated by purification. For this purpose, the lysate may be (i) treated to remove nucleic acids. e.g., by polymin precipitation;
(ii) concentrated in the presence of arginine, e.g., by centrifugation and/or ultrafiltrated in a buffer containing arginine, e.g., 250 to 320 mM arginine; and/or
(iii) purified by chromatography methods, e.g., by means of cation exchange chromatography and, optionally, by anion exchange chromatography.

In a more preferred embodiment, the lysate is
(i) treated to remove nucleic acids, e.g., by polymin precipitation;
(ii) concentrated in the presence of arginine, e.g., by centrifugation and/or ultrafiltrated in a buffer containing arginine, e.g., 250 to 320 mM arginine; and
(iii) purified by chromatography methods, e.g., by means of cation exchange chromatography and, optionally, by anion exchange chromatography.

The following Figures and Examples are intended to illustrate various embodiments of the invention. As such, the specific modifications discussed are not to be construed as limitations on the scope of the invention. It will be apparent to the person skilled in the art that various equivalents, changes, and modifications may be made without departing from the scope of the invention, and it is thus to be understood that such equivalent embodiments are to be included herein.

SPECIFIC EMBODIMENTS

Example 1

Test for Enzymatic Activity of Alpha-Galactosidase

The enzymatic activity of alpha-galactosidase was measured essentially as previously described (Liu et al., 2007). As a synthetic substrate, 4-Nitrophenyl-α-D-galactoside was used. The release of p-Nitro-phenol was followed at a wavelength of 405 nm in a reaction buffer containing 100 mM sodium phosphate, 50 mM sodium chloride, pH 6.8 at 26° C.

Example 2

Screening for Additives

A variety of additives was tested to improve the solubility of partially purified alpha-galactosidase. The supernatant of the polymine precipitation step (see Example 5 below) was used as sample.

In detail, a variety of buffers containing a buffer substance (50 mM Tris, 20 mM sodium chloride, pH 7.0) and additives at different concentrations were prepared (Table 1). Aliquots of the supernatant containing about 20 mg/ml protein were diafiltrated at room temperature against the respective buffers. During the diafiltration step the appearance of the alpha-galactosidase solution was monitored by visual inspection of the samples. In most of the samples, a precipitation of alpha-galactosidase occurred during diafiltration.

Common additives like, e.g., detergents, urea and sugars failed to solubilize the enzyme. As shown in Table 1, L-arginine was found to be the preferred additive keeping the enzyme in solution.

Table 1 shows the influence of additives on the solubility of alpha-galactosidase.

| Additive | Concentration | Appearance |
| --- | --- | --- |
| Glycerol [%] | 1.0 | white precipitate (wp) |
| | 3.0 | wp |
| | 5.0 | wp |
| | 10.0 | wp |
| MgCl₂ [mM] | 1.0 | wp |
| | 5.0 | wp |
| | 10.0 | wp |
| | 20.0 | wp |

-continued

| Additive | Concentration | Appearance |
| --- | --- | --- |
| Glycopon [%] | 0.1 | wp |
| | 1.0 | wp |
| | 5.0 | wp |
| | 10.0 | wp |
| DTT [mM] | 1.0 | wp |
| | 5.0 | wp |
| | 10.0 | wp |
| | 20.0 | wp |
| Polymine P [%] | 0.01 | wp |
| | 0.1 | wp |
| | 0.5 | wp |
| | 1.0 | wp |
| Tween 20 [%] | 0.1 | wp |
| | 0.5 | wp |
| | 1.0 | wp |
| | 2.0 | wp |
| Nonidet P40 [%] | 0.1 | wp |
| | 0.5 | wp |
| | 1.0 | wp |
| | 2.0 | less precipitate |
| BSA [µg/ml] | 1.0 | wp |
| | 10.0 | wp |
| | 100.0 | wp |
| | 1000.0 | less precipitate |
| Urea [mM] | 1.0 | wp |
| | 10.0 | wp |
| | 50.0 | wp |
| | 100.0 | wp |
| Raffinose | 0.25 | wp |
| | 0.5 | wp |
| | 1.0 | wp |
| | 2.0 | wp |
| Sucrose | 0.1 | wp |
| | 0.5 | wp |
| | 1.0 | wp |
| | 2.0 | wp |
| D,L-Glycine [mM] | 1.0 | wp |
| | 10.0 | wp |
| | 50.0 | wp |
| | 100.0 | wp |
| L-Arginine [mM] | 0.1 | wp |
| | 1.0 | wp |
| | 10.0 | wp |
| | 100.0 | slightly opal solution |
| | 150.0 | clear solution |
| | 200.0 | clear solution |

As demonstrated by the results shown in Table 1, alpha-galactosidase was stabilized only in the presence of arginine at a final concentration of above 100 mM, such as at least 150 mM.

Example 3

Screening of Buffer Conditions

To characterize the solubility of alpha-galactosidase, different buffer conditions were studied. For that purpose, the supernatant of the polyamine precipitation step (see Example 5) was used as a sample. A range of pH 4.5 to pH 9.5 was tested in 50 mM sodium phosphate buffer As indicated in Table 2, different conductivities were also studied. The conductivity was adjusted by the addition of aliquots of a sodium chloride stock solution to the respective buffer solution. The appearance of the alpha-galactosidase solution was monitored by visual inspection of the samples. As shown in Table 2, the enzyme precipitated under acidic and neutral buffer conditions (pH values of less than pH 7.5). It remained in solution at higher pH values. The conductivity of the buffer did not affect the solubility under the conditions tested.

Table 2 shows the influence of pH and conductivity on the solubility of alpha-galactosidase.

| pH | Conductivity [mS] | Appearance |
|---|---|---|
| 4.50 | 6.00 | white precipitate |
| 5.50 | 6.00 | white precipitate |
| 6.50 | 6.00 | white precipitate |
| 7.50 | 6.00 | white precipitate |
| 7.50 | 15.00 | white precipitate |
| 8.00 | 6.00 | opal solution |
| 8.00 | 15.00 | opal solution |
| 8.50 | 15.00 | opal solution |
| 9.00 | 6.00 | clear solution |
| 9.50 | 15.00 | clear solution |

The result shown in Table 2 indicate that the protein is kept is solution at a pH of 9.0 or 9.5. However, it was found that the protein looses activity at higher pH values.

Example 4

Protein Measurement

The protein concentration of the respective fractions and pools were determined by measuring the protein absorbance at 280 nm. The measurement of protein concentration is a standard method known in the art. For the recombinant alpha-galactosidase, a molecular extinction coefficient of 1.279 was used to calculate the concentration of the enzyme.

Example 5

Preparation of Alpha-Galactosidase (B-Zyme)

*E. coli* HB101 cells which overexpressed recombinant alpha-galactosidase were used as the starting material to prepare a stabilized composition of alpha-galactosidase (B-zyme). The preparation was carried out by means of ultrafiltration, and by a subsequent dialysis step after cell lysis and separation of nucleic acids. The preparation process yields a stable composition of the recombinant alpha-galactosidase enzyme (B-zyme) which can be stored or used for further purification procedures.

The following buffers were used:
Buffer A: 50 mM Tris/HCl, 20 mM NaCl, pH 7.5+/−0.2 (6 mS/cm+/−0.1)
Buffer B: 50 mM sodium phosphate, 310 mM L-Arginine, pH 6.0+/−0.2 (20 mS/cm+/−0.1)

Cell Lysis:
3.6 l of buffer A were added to 260 g of frozen *E. coli* cells (dry mass; equivalent to about 1000 g of wet weight). The cells were thawed and suspended. Subsequently the cells were lysed by means of an APV high pressure device (at 750-800 bar) while cooling the suspension on ice. The following steps of the purification procedure were done at room temperature.

Precipitation of Nucleic Acids:
After cell lysis, the nucleic acids present in the crude extract were removed by means of polymin precipitation. For that purpose, a portion of 3 M sodium chloride (10% of the volume) was added to the extract to a final concentration of 300 mM. If necessary, the pH value was readjusted to pH 7.5±0.2 using either 4 N NaOH or 4 N HCl. Then, a polymin P solution (10%) was added stepwise until complete precipitation of the nucleic acids was achieved. Afterwards, the solution was centrifuged for 10 min at 5000 rpm. The obtained supernatant was optionally stored at 4° C. for over night before it was subjected to a further concentration step.

Concentration & Ultrafiltration (i.e. Diafiltration):
The clear supernatant obtained after the centrifugation step (i.e. the polymin P supernatant) typically has a protein concentration of 20-30 mg/ml. The supernatant was concentrated by using the Am icon Ultra 4 (Millipore, Mass., USA) membrane. The concentrated polymin P supernatant was optionally stored at 4° C. The supernatant was then diafiltrated by means of an ultrafiltration device. For that purpose, a 30 kDa membrane (e.g., Pellicon 2, Millipore, Mass., USA) was used. The solution was first concentrated using a 30 kDa Membran (e.g., Pellicon 2, Millipore, USA) and then extensively dialysed (diafiltrated) against 5 volumes of buffer B (pH adjusted with HCl 25%). The result of the dialysis step is a stabilized composition of alpha-galactosidase having a specific activity of 0.5-0.8 U/mg.

Due to the addition of arginine, diafiltration of the composition comprising alpha-galactosidase is possible without precipitation of the protein. The procedure as set forth above also enables the further purification of the protein via ion-exchange chromatography on Poros HS 50 (Applied Biosystems, Darmstadt, Germany).

Example 6

Purification of Alpha-Galactosidase (B-Zyme)

The purification was carried out by means of chromatographic methods. Two consecutive chromatographies were performed. In the first chromatography step, the alpha-galactosidase is bound to cation exchange resin and eluted from the column by a high-salt treatment. In the second chromatography step, the enzyme is applied to an anion exchange resin and obtained in the flow through. The purification process yields the recombinant alpha-galactosidase enzyme in a highly purified quality.

The following buffers were used:
Buffer C: 50 mM sodium phosphate, 0.043 M L-Arginine, pH 6.0+/−0.2 (7 mS/cm+/−0.1)
Buffer D: 50 mM sodium phosphate, 0.043 M L-Arginine, 350 mM NaCl; pH 6.0+/−0.2 (40 mS/cm+/−0.1)
Buffer E: 20 mM Tris/HCl, 60 mM NaCl, pH 8.0/−0.2 (7.5 mS/cm+/−0.1)
Buffer F: 25 mM sodium phosphate, 0.3 M NaCl, pH 7.0+/−0.2 (>30 mS/cm).

All indicated pH values are defined to comprise a deviation of +/−0.2 pH units.

Chromatography on Poros HS 50 (Cation-Exchange Chromatography):
A Poros FIS. 50 column (5 l, Applied Biosystems, Darmstadt, Germany) was equilibrated with buffer C. The stabilized alpha-galactosidase composition obtained as described in Example 5 was loaded onto the column. The Poros HS 50 column as used in the present invention can be loaded with 0.2-1 g of protein/33 ml of ion exchange material.

The column was washed using buffer C. After the washing step the enzyme was eluted by using buffer D. The enzyme eluted in a single peak. In the relevant fractions enzyme activity and protein concentration was determined. Fractions containing the recombinant alpha-galactosidase were pooled.

Ultrafiltration:
The pool of fractions containing the enzyme was diafiltrated by means of an ultrafiltration device. A 30 kDa membrane (e.g., Pellicon 2, Millipore, USA) was used. The protein solution was extensively dialysed against buffer E. The protein solution was optionally stored at 4° C. before further processing.

Figure 1:
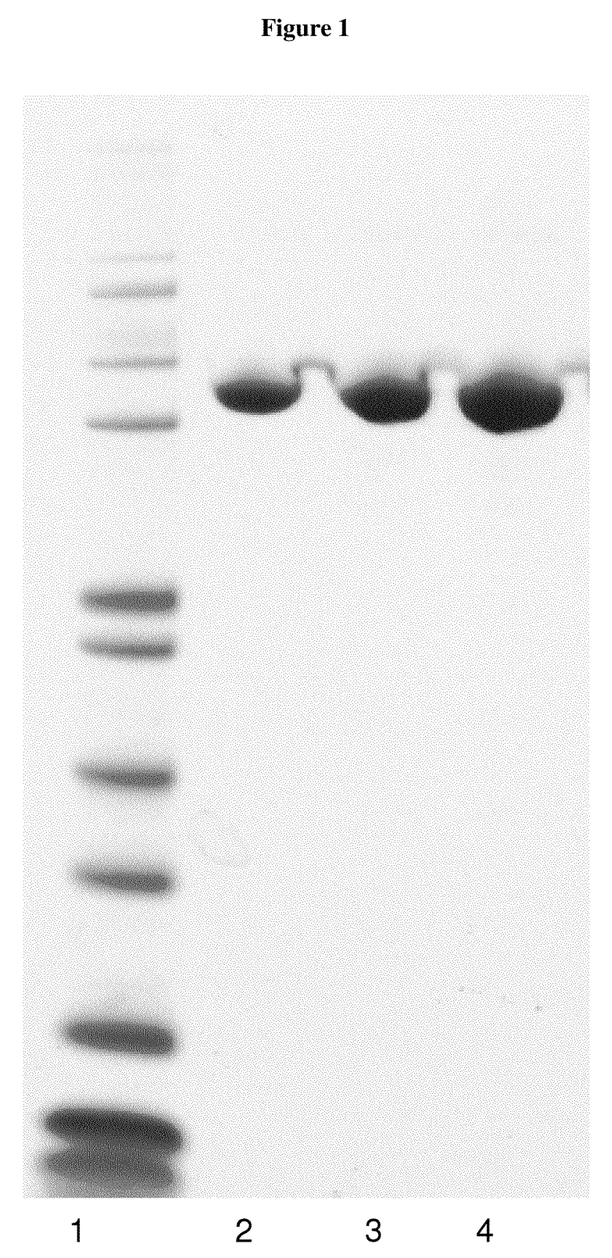
FIG. 1 shows the purified alpha-galactosidase protein obtained by the method of the present invention after separation on a 4-20% Tris/glycine SDS polyacrylamide gel using standard gel electrophoresis. The purified protein was visualized by staining of the gel with Coomassie Blue (SIMPLY BLUE, Invitrogen, CA, USA). Running Buffer: Mes 1x; Marker: Mark 12 (Invitrogen, CA, USA).
  Lane 1: Molecular weight marker (Mark 12, Invitrogen, CA, USA)
  Lane 2: 3 µg of alpha-galactosidase (B-zyme)
  Lane 3: 4.5 µg of alpha-galactosidase (B-zyme)
  Lane 4: 9 µg of alpha-galactosidase (B-zyme)
Figure 2:
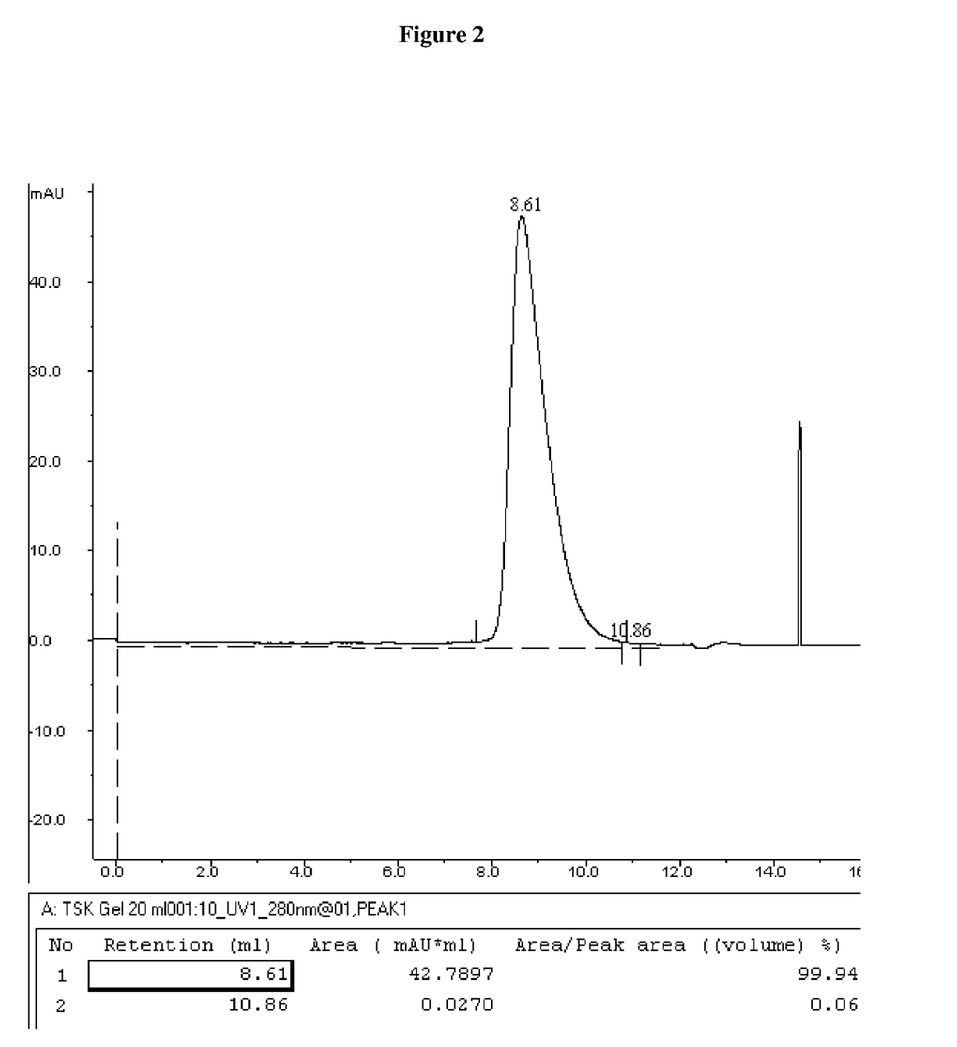
FIG. 2 shows the HPLC analysis is of purified alpha-galatosidase (B-zyme).
  100 µg protein sample (1.5 mg/ml protein) was applied onto a TSK 3000 (Tosoh Bioscience GmbH, Stuttgart, Germany) column.

Chromatography on Q Sepharose Fast Flow (Anion-Exchange Chromatography):

The dialysed pool was applied onto a Q Sepharose fast flow column (500 ml, Amersham Bioscience, Uppsala, Sweden) which was equilibrated with 2 column volumes of buffer E. At most, a maximal concentration of 40 mg protein per ml of ion exchange resin should be applied to the column. The column was washed using buffer E. Fractions were collected and monitored for alpha-galactosidase activity. Aliquots of the fractions were taken, analyzed for activity and visualized by SUS polyacrylamide, gel electrophoresis. The recombinant alpha-galactosidase eluted in the flow through. Fractions showing a pure band of alpha-galactosidase with a molecular weight of 64.5 kDa were pooled and dialysed against the storage buffer (buffer F). As shown by SDS gel electrophoresis, the enzyme preparation is pure (FIG. 1). In HPLC analysis, a purity of >99% was determined for the enzyme preparation (FIG. 2).

Example 7

SDS Gel Electrophoresis

SDS gel electrophoresis was carried out using commercially available gels (4-20%, Invitrogen, CA, USA). After running the gel, proteins were detected by staining with Coomassie Blue (SIMPLY BLUE, Invitrogen, CA, USA). A molecular weight marker (Mark 12, Invitrogen, CA, USA) was used to determine the apparent molecular weight of the proteins. The results are shown in FIG. 1.

Example 8

Analytical HPLC

Analytical HPLC was used to determine the purity of the protein tractions and pools. Aliquots (100 µl) were applied onto a TSK G3000 SW (Tosoh Bioscience GmbH, Stuttgart, Germany). The column was run in an appropriate buffer (50 mM Tris/HCl, 100 mM NaCl, pH 7.5). Proteins were detected by measuring the absorbance at 280 nm. The results are shown in FIG. 2.

What is claimed is:

1. An aqueous composition comprising a protein with enzymatic activity of alpha-galactosidase, the composition further comprising arginine at a concentration of above 100 mM, wherein the composition has a conductivity of at most 40 mS/cm.

2. The composition of claim 1 wherein the concentration of arginine is at least 150 mM.

3. The composition of claim 1 wherein the concentration of arginine is between 150 mM and 2 M.

4. The composition of claim 1 wherein the concentration of arginine is between 200 and 400 mM.

5. The composition of claim 1 wherein the concentration of arginine is between 250 mM and 320 mM.

6. The composition of claim 1 further wherein the composition has a conductivity of between 15 mS/cm and 25 mS/cm.

7. The composition of claim 1 further wherein the composition has a conductivity of between 18 mS/cm and 22 mS/cm.

8. The composition of claim 1 wherein the composition has a pH between 5 and 7.5.

9. The composition of claim 1 wherein the composition has a pH between 5.5 and 7.

10. The composition of claim 1 wherein the composition has a pH between 5.8 and 6.5.

11. The composition of claim 1 wherein the composition is derived from a bacterial host cell.

12. The composition of claim 11 wherein the bacterial host cell is *E. coli*.

13. The composition of claim 1 further wherein the total protein content of the composition is at least 20 mg/ml.

14. The composition of claim 1 further wherein the enzymatic activity of alpha-galactosidase is between 0.5 and 0.8 units/mg of total protein.

15. The composition of claim 1 wherein the protein has a substrate specificity of EC 3.2.1.22.

16. The composition of claim 1 wherein the protein hydrolyses terminal alpha-1,3-galactosyl moieties.

17. The composition of claim 1 wherein the protein is a naturally occurring protein or a functionally active derivative or fragment thereof.

18. The composition of claim 17 wherein the naturally occurring protein is derived from an organism selected from the group consisting of human, animal, plant, fungi, and bacteria.

19. The composition of claim 18 wherein the bacteria is *Bacteroides fragilis*.

20. The composition of claim 19 wherein the *Bacteroides fragiles* comprises the amino acid sequence of SEQ ID NO: 1.

21. A method of stabilizing an aqueous composition comprising a protein with enzymatic activity of alpha-galactosidase, the method comprising the steps of adding arginine to the composition to a final concentration of above 100 mM and maintaining conductivity of the composition to at most 40 mS/cm.

22. The method of claim 21 wherein the final concentration is at least 150 mM.

23. A method of preparing a purified aqueous composition comprising a protein with enzymatic activity of alpha-galactosidase and having a conductivity of at most 40 mS/cm, the method comprising the steps of providing a composition containing the protein, concentrating the composition in the presence of arginine to an arginine concentration of above 100 mM, and purifying the concentrated composition via cation exchange chromatography.

24. The method of claim 23 wherein the concentration of arginine is at least 150 mM.

25. The method of claim 23 wherein the concentration of arginine is between 150 mM and 2M.

26. The method of claim 23 wherein the concentration of arginine is between 200 and 400 mM.

27. The method of claim 23 wherein the concentration of arginine is between 250 mM and 320 mM.

28. The method of claim 23 wherein the method further comprises an additional purification step performed before or after the concentration step.

* * * * *